United States Patent
Hur et al.

(10) Patent No.: US 9,757,496 B2
(45) Date of Patent: Sep. 12, 2017

(54) THERMALLY HEALABLE AND RESHAPABLE CONDUCTIVE HYDROGEL COMPOSITE

(71) Applicants: SAMSUNG ELECTRONICS CO., LTD., Suwon-si (KR); KOREA ADVANCED INSTITUTE OF SCIENCE AND TECHNOLOGY, Daejeon-si (KR)

(72) Inventors: Jae-hyun Hur, Yongin-si (KR); No-kyoung Park, Hwaseong-si (KR); Kyu-hyun Im, Yongin-si (KR); Sang-won Kim, Seoul (KR); Sung-woo Hwang, Seoul (KR); Jang-wook Choi, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

( * ) Notice: Subject to any disclaimer, the term of this patent is extended or adjusted under 35 U.S.C. 154(b) by 37 days.

(21) Appl. No.: 14/463,884

(22) Filed: Aug. 20, 2014

(65) Prior Publication Data
US 2015/0053896 A1    Feb. 26, 2015

(30) Foreign Application Priority Data
Aug. 26, 2013    (KR) .................. 10-2013-0101278

(51) Int. Cl.
*A61L 27/60*    (2006.01)
*H01B 1/22*    (2006.01)
(Continued)

(52) U.S. Cl.
CPC ............... *A61L 27/60* (2013.01); *A61L 27/20* (2013.01); *A61L 27/443* (2013.01);
(Continued)

(58) Field of Classification Search
None
See application file for complete search history.

(56) References Cited

U.S. PATENT DOCUMENTS 6,471,993 B1 * 10/2002 Shastri ................ A61K 9/1647
424/422
7,737,240 B2    6/2010 Marks et al.
(Continued)

FOREIGN PATENT DOCUMENTS

JP    5458264 B2    4/2014

OTHER PUBLICATIONS

Syed K. H. Gulrez, Saphwan Al-Assaf and Glyn O Phillips (2011). Hydrogels: Methods of Preparation, Characterisation and Applications, Progress in Molecular and Environmental Bioengineering—From Analysis and Modeling to Technology Applications, Prof. Angelo Carpi (Ed.), ISBN: 978-953-307-268-5, InTech, DOI: 10.5772/24553. pp. 117-150.*

(Continued)

*Primary Examiner* — Katie L Hammer
(74) *Attorney, Agent, or Firm* — Sughrue Mion, PLLC

(57) ABSTRACT

An electro-conductive hydrogel composite material that may be suitable as an artificial skin satisfies all four requirements of artificial skin, namely, flexibility, electrical conductivity, healing property, and biocompatibility. The electro-conductive hydrogel composite material includes a hydrogel composition including water and a cross-linkable polymer which reversibly forms cross-linkage by hydrogen bonding; and an electro-conductive material dispersed in the hydrogen bond-based hydrogel.

20 Claims, 8 Drawing Sheets

(51) Int. Cl.

| | | |
|---|---|---|
| *A61L 27/50* | (2006.01) | |
| *A61L 27/48* | (2006.01) | |
| *A61L 27/52* | (2006.01) | |
| *B82Y 5/00* | (2011.01) | |
| *C08J 3/24* | (2006.01) | |
| *C08J 3/075* | (2006.01) | |
| *A61L 27/20* | (2006.01) | |
| *A61L 27/44* | (2006.01) | |

(52) U.S. Cl.
CPC ............ *A61L 27/446* (2013.01); *A61L 27/48* (2013.01); *A61L 27/50* (2013.01); *A61L 27/52* (2013.01); *B82Y 5/00* (2013.01); *C08J 3/075* (2013.01); *C08J 3/247* (2013.01); *H01B 1/22* (2013.01)

(56) References Cited

U.S. PATENT DOCUMENTS

| | | | |
|---|---|---|---|
| 8,304,247 B2 | 11/2012 | Peppas et al. | |
| 2008/0083908 A1* | 4/2008 | Jang ................... | H01B 1/22 252/500 |
| 2008/0213389 A1* | 9/2008 | Lelkes ................ | A61K 35/12 424/572 |
| 2011/0230816 A1* | 9/2011 | Copp-Howland ... | A61K 9/0009 604/20 |
| 2011/0257504 A1* | 10/2011 | Hendricks ............ | A61B 5/0408 600/395 |
| 2012/0100217 A1* | 4/2012 | Green .................. | H01B 1/122 424/487 |
| 2012/0237557 A1* | 9/2012 | Lewitus ............... | B82Y 5/00 424/400 |
| 2012/0316631 A1 | 12/2012 | Axelgaard | |
| 2013/0006339 A1 | 1/2013 | March et al. | |
| 2013/0006355 A1 | 1/2013 | Iriyama et al. | |
| 2013/0018334 A1 | 1/2013 | Glynn et al. | |
| 2013/0030341 A1 | 1/2013 | Freer et al. | |
| 2013/0041235 A1 | 2/2013 | Rogers et al. | |

OTHER PUBLICATIONS

Bronzino, Joseph D., ed. (2006). Biomedical Engineering Handbook—Biomedical Engineering Fundamentals (3rd Edition). (pp. 37-1 to 37-3). Taylor & Francis. Online version available at: http://app.knovel.com/hotlink/toc/id:kpBEHBEFE4/biomedical-engineering/biomedical-engineering.*
Lipomi, et al.; "Skin-like pressure and strain sensors based on transparent elastic films of carbon nanotubes"; Nature Technology; vol. 6; Dec. 2011; pp. 788-792.
Nakahata, et al.; "Redox-responsive self-healing materials formed from host-guest polymers"; Nature Communications; Oct. 2011; vol. 2 No. 511; 6 pages total.
Shepherd et al.; Multigait soft robot; PNAS; Dec. 20, 2011; vol. 108 No. 51; pp. 20400-20403.
Zhenqiang Ma; "An Electronic Second Skin"; Science; vol. 333; Aug. 12, 2011; pp. 830-831.
Tee et al.; "An electrically and mechanically self-healing composite with pressure- and flexion-sensitive properties for electronic skin applications"; Nature Technology; Nov. 11, 2012; vol. 7; pp. 825-832.
Chen et al.; "A Thermally Re-mendable Cross-Linked Polymeric Material"; Science vol. 295; Mar. 1, 2002; pp. 1698-1702.
Odom, et al.; "A Self-healing Conductive Ink"; Advanced Materials; 2012; vol. 24; pp. 2578-2581.
Phadke, et al.; "Rapid self-healing hydrogels"; PNAS; Mar. 20, 2012; vol. 109 No. 12; pp. 4383-4388.
Takei et al.; " Nanowire active-matrix circuitry for low-voltage macroscale artificial skin"; Nature Materials; Sep. 12, 2010; vol. 9; 10 pages total.
"Highly Sensitive Flexible Pressure Sensors with Micro-structured Rubber Dielectric Layers"; Science Highlight; Oct. 2011; 4 pages total.

* cited by examiner (a)          (b)          (c)

(a)          (b)

(a)  (b)

THERMALLY HEALABLE AND RESHAPABLE CONDUCTIVE HYDROGEL COMPOSITE

CROSS-REFERENCE TO RELATED APPLICATION

This application claims priority from Korean Patent Application No. 10-2013-0101278, filed on Aug. 26, 2013, in the Korean Intellectual Property Office, the disclosure of which is incorporated herein by reference in its entirety.

BACKGROUND

1. Field

The present disclosure relates to artificial skin or electronic skin. The present disclosure relates to conductive hydrogel.

2. Description of the Related Art

Biological skin has the ability to sense external stimulations, the ability to repeatedly heal injuries, and flexibility to adapt to motions of muscles. Research is being conducted from various vantage points to obtain artificial skin that imitates such biological skin.

Requirements of the artificial skin include the following four requirements: first, in terms of mechanical property, "flexibility" to adapt to motions of muscles is required. Flexibility may be measured by Young's modulus. Second, in terms of functionality, "electrical conductivity" is needed to transmit electrical signals generated from external stimulations. Third, "healing property" is required. Healing property refers to the ability to repeat an injury-healing cycle many times. Fourth, in terms of a biological property, "biocompatibility" is required. Biocompatibility refers to bio-friendliness (i.e., the quality of not having toxic or injurious effects on biological systems) of materials used in the artificial skin.

An example of conventional artificial skin is a flexible substrate with an electronic device (for example, a capacitor or a transistor) embedded on the flexible substrate. See, "Nature Mater. (2010), 9, 859, Stanford"; "Nature Mater. (2010), 9, 821, Berkeley," and "Nature Nanotech. (2011), 6, 788, Stanford." However, in this case, although the requirements of mechanical property and functionality are satisfied, the requirements of healing property and biocompatibility are not satisfied.

Other example of the artificial skin is hydrogel or a synthetic polymer having healing properties. See, "Science (2002), 295, 1698, UCLA & USC," "PNAS (2012), 109, 4383, UCSD," and "Nature Comm (2011), 2, 1, Osaka.". However, in this case, the requirements of healing property and biocompatibility may be satisfied, but the requirements of mechanical property and functionality are not satisfied.

Another example of the conventional artificial skin is a material that may self-heal injured portions to recover electrical properties. See, "Nature Nanotech (2012), Online, Stanford"; and "Adv. Mater. (2012), 24, 2578." However, in this case, the requirements of mechanical property, functionality, and healing property may be satisfied, but the requirement of biocompatibility is not satisfied.

Another example of the conventional artificial skin is obtained by directly embedding various sensors onto biological skin. See, "PNAS (2011), Harvard" and "Science (2011), 333, 830, URIC." However, in this case, the requirements of mechanical property and functionality may be satisfied, but the requirements of healing property and biocompatibility are not satisfied.

Accordingly, conventional artificial skin candidates only satisfy one to three requirements of the four requirements of artificial skin.

SUMMARY

Provided is an electro-conductive hydrogel composite material that may be used as a new candidate for artificial skin, which satisfies all four requirements of artificial skin, namely, "flexibility," "electrical conductivity," "healing property," and "biocompatibility."

Additional aspects will be set forth in part in the description which follows and, in part, will be apparent from the description, or may be learned by practice of the presented embodiments.

According to an aspect of the present disclosure, an embodiment of an electro-conductive hydrogel composite material includes a hydrogen bond-based hydrogel including water and a cross-linkable polymer capable of being cross-linked by hydrogen bonding; and an electro-conductive material dispersed in the hydrogen bond-based hydrogel.

According to another aspect of the present disclosure, an embodiment of preparing an electro-conductive hydrogel composite material includes cooling a heated dispersion liquid including a cross-linkable polymer capable of being cross-linked by hydrogen bonding, water, and an electro-conductive material.

According to another aspect of the present disclosure, an embodiment of preparing an electro-conductive hydrogel composite material containing a hydrogen bond-based hydrogel comprising water and a cross-linkable polymer capable of being cross-linked by hydrogen bonding; and an electro-conductive polymer dispersed in the hydrogen bond-based hydrogel include a step of cooling a heated reaction mixture comprising the cross-linkable polymer capable of being cross-linked by hydrogen bonding; water; a monomer for forming an electro-conductive polymer; and an oxidizing agent.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
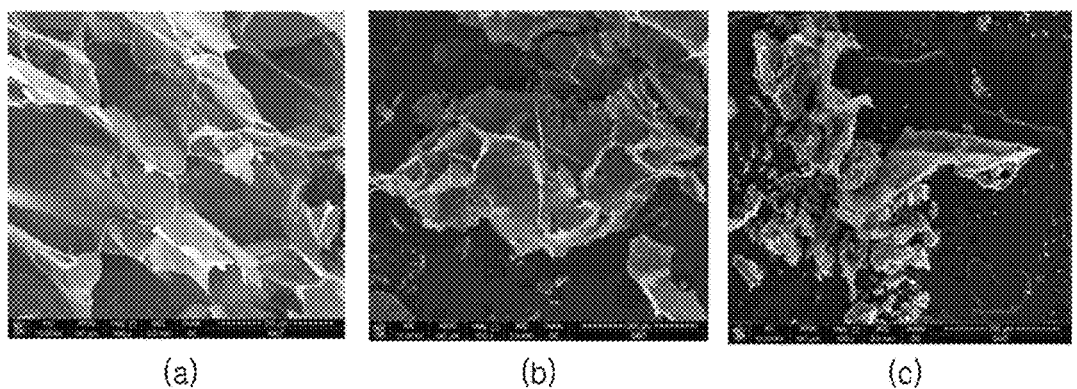
FIG. 1(a)-1(c) are scanning electron microscope (SEM) images of freeze-dried (a) agarose hydrogel of Comparative Example 1, (b) electro-conductive hydrogel composite material of Example 2, and (c) electro-conductive hydrogel composite material of Example 1.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Hereinafter, an embodiment of an electro-conductive hydrogel composite material according to an aspect of the present disclosure will be described in greater detail. An embodiment of the electro-conductive hydrogel composite material according to an aspect of the present disclosure includes a hydrogen bond-based hydrogel including water and a cross-linked polymer cross-linked by hydrogen bonding; and an electro-conductive material dispersed in the hydrogen bond-based hydrogel.

A hydrogel is known to be formed from a mixture of water and a cross-linkable polymer. When water and the cross-linkable polymer forms a cross-linked network, the mixture of water and the cross-linked polymer becomes gels, which is a hydrogel. The hydrogel used in the present disclosure is a hydrogel formed from across-linked polymer of which cross-linkage formed by hydrogen bonding (simply referred to as a "hydrogen bond-based hydrogel").

Cross-linkage by hydrogen bonding is reversible. When the hydrogen bond-based hydrogel is heated, hydrogen bonds between and/or within polymer chains break down, and accordingly, the cross-link network is disassembled, thereby forming a liquid with fluidity (for example, a colloid, a sol, or an aqueous solution). When the liquid with fluidity is cooled, hydrogen bonds between and/or within the polymer chains are re-formed, and accordingly, the cross-linkage network is recovered, thereby forming a hydrogel that lacks fluidity.

Due to the reversibility of the hydrogen bond cross-linkage, the electro-conductive hydrogel composite material of the present disclosure may have a healing property. In other words, the electro-conductive hydrogel composite material of the present disclosure is thermally healable. In greater detail, when an electro-conductive hydrogel composite material having defects is heated, a cross-link network of the electro-conductive hydrogel composite material disassembles, and thus, the electro-conductive hydrogel composite material of the present disclosure becomes to have fluidity. Due to this fluidity, the defects of the electro-conductive hydrogel composite material are filled. Then, when the electro-conductive hydrogel composite material of the present disclosure is cooled again, the electro-conductive hydrogel composite material re-gels to form a hydrogel which is free of defects.

The cross-linkable polymer capable of being cross-linked by hydrogen bonds may be, for example, agarose.

The hydrogen bond-based hydrogel may have "flexibility" similar to biological skin. Also, the hydrogen bond-based hydrogel according to an embodiment is a bio-based material or a non-toxic material, and thus, has biocompatibility.

In the hydrogen bond-based hydrogel, an amount of water may be, for example, about 0.5 parts by weight to about 5.0 parts by weight based on 100 parts by weight of the cross-linked polymer of which cross linkage is formed by hydrogen bond (hereinafter, simply "cross-linked polymer" or "polymer"). When the amount of water in the hydrogen bond-based hydrogel is too high, the viscosity of a hydrogen bond-based hydrogel solution may be too low, and thus, the density of hydrogen bonds in the cross-linked polymer may be too low to form a hydrogel. When the amount of water in the hydrogen bond-based hydrogel is too low, the viscosity of the hydrogen bond-based hydrogel solution may be too high, and thus, the density of hydrogen bonds in the resulting hydrogen bond-based hydrogel may be too high, and the hydrogel may not be dissolved.

An electro-conductive material is dispersed in the hydrogen bond-based hydrogel. The electro-conductive material may form an electro-conductive network in the hydrogen bond-based hydrogel. Accordingly, the hydrogel composite material of the present disclosure has "electrical conductivity."

The electro-conductive material may be, for example, a metal particle, a conductive carbon material, a conductive polymer, or a combination thereof.

The metal particle may be, for example gold (Au), silver (Ag), platinum (Pt), titanium (Ti), iron (Fe), or a combination thereof. The metal particle is harmless to humans.

The conductive carbon material may be, for example, carbon black, carbon nanotubes, graphene, or a combination thereof.

The conductive polymer may be, for example, polypyrroles, poly(3,4-ethylenedioxythiophenes, poly(styrenesulfonates), poly(3,4-ethylenedioxythiophenes):poly(styrenesulfonates) (PEDOT:PSS), polyaniline, or a combination thereof.

For example, the electro-conductive material may exist in a particle form in the hydrogen bond-based hydrogel. The electro-conductive material may have, for example, an average particle size of about 100 nm to about 1 μm.

An amount of the electro-conductive material dispersed in the hydrogen bond-based hydrogel may be, for example, about 10 parts by weight to about 300 parts by weight based on 100 parts by weight of the polymer. When the amount of the electro-conductive material is too small, the hydrogel may not have conductivity. When the amount of the electro-conductive compound is too large, the hydrogel may lose gel properties.

Due to the electro-conductive material dispersed in the hydrogen bond-based hydrogel, the hydrogel composite material of the present disclosure has electrical conductivity. The electrical conductivity of the hydrogel composite material of the present disclosure may be, for example, about $1.0 \times 10^{-6}$ S/cm to about 0.2 S/cm, when measured by a 4-point probe method under standard conditions (a temperature of 25° C., pressure of 1 atm-absolute).

According to another embodiment of the electro-conductive hydrogel composite material, water in hydrogen bond-based hydrogel may further include an electrolyte. When the water in the hydrogen bond-based hydrogel further includes an electrolyte, the electrolyte may undergo synergism (for example, electron/hole current from the electro-conductive polymer and ion current from the electrolyte combine to induce synergism) with the electro-conductive material dispersed in the hydrogen bond-based hydrogel to further improve the electrical conductivity of the hydrogel composite material.

Embodiments of the electro-conductive hydrogel composite material, in which water in the hydrogen bond-based hydrogel further includes an electrolyte, may have a higher electrical conductivity by about 0.22 S/cm to about 0.69 S/cm than the embodiments of the electro-conductive hydrogel composite material in which water in the hydrogen bond-based hydrogel does not include electrolyte.

The electrolyte may be, for example, NaCl, KCl, $Na_2HPO_4$, $KH_2PO_4$, $Na_2SO_4$, $Li_2SO_4$, $MgSO_4$, a buffer (for example, PBS or Tris-HCl), or a combination thereof. An amount of the electrolyte may be, for example, about 0.1 parts by weight to about 5.0 parts by weight based on 100 parts by weight of water in the hydrogen bond-based hydrogel. In greater detail, water in the hydrogen bond-based hydrogel may be phosphate-buffered saline (PBS). The PBS may be, for example, a mixture of NaCl, KCl, $Na_2HPO_4$, $KH_2PO_4$, and water. The PBS may be, for example, 10×PBS or 1×PBS. A composition of 1 L of the 10×PBS may include, for example, 80 g of NaCl, 2 g of KCl, 14.4 g of $Na_2HPO_4$, 2.4 g of $KH_2PO_4$, and a residual amount of water. A composition of the 1 L of 1×PBS may include, for example, 8 g of NaCl, 0.2 g of KCl, 1.44 g of $Na_2HPO_4$, 0.24 g of $KH_2PO_4$, and a residual amount of water.

In another embodiment of the electro-conductive hydrogel composite material, the electro-conductive material is polypyrrole, and an amount of the polypyrrole is about 300 parts by weight or less based on 100 parts by weight of the polymer. When the amount of the polypyrrole is greater than 300 parts by weight, the number of repetitions of a thermal healing cycle decreases dramatically. When the amount of the polypyrrole is about 10 parts by weight or less based on 100 parts by weight of the cross-linked polymer, the electro-conductive hydrogel composite material may be cooled to re-form the gel even after 10 thermal healing cycles. However, when the amount of the polypyrrole is greater than 50 parts by weight based on 100 parts by weight of the polymer, the electro-conductive hydrogel composite material is no longer capable of forming a gel after 4 repetitions at most. It is speculated that when the amount of the polypyrrole exceeds a certain amount, hydrogen bonding sites of the polymer become blocked by the polypyrroles.

According to an embodiment of the present disclosure, a method of preparing an electro-conductive hydrogel composite material includes cooling a heated dispersion liquid including a polymer, water, and an electro-conductive material.

The water may further include an electrolyte.

A heating temperature of the dispersion liquid may be, for example, about 110° C. to about 150° C. When the heating temperature of the dispersion liquid is too low, the hydrogel may not be sufficiently transform into a fluidic liquid. When the heating temperature of the dispersion liquid is too high, the water may evaporate without sufficiently dissolve the hydrogel.

A cooling temperature of the dispersion liquid may be, for example, about 25° C. or lower. The cooling temperature of the dispersion liquid may be higher or lower than 25° C., as long as the hydrogel does not dissolve, i.e., transform into a fluidic state.

According to another aspect of the present disclosure, there is provided an embodiment of a method of preparing an electro-conductive hydrogel composite material that includes water and a hydrogen bond-based hydrogel including a cross-linkable polymer which is capable of forming intra and inter-chain cross linkage by hydrogen bonding; and an electro-conductive polymer dispersed in the hydrogen bond-based hydrogel, the method including cooling a heated reaction mixture including the cross-linkable polymer; water; a monomer for forming an electro-conductive polymer; and an oxidizing agent.

The water may further include an electrolyte.

The monomer for forming an electro-conductive polymer may be, for example, a monomer for forming polypyrroles, a monomer for forming poly(3,4-ethylenedioxythiophenes), a monomer for forming poly(styrenesulfonates), a monomer for forming PEDOT:PSS, or a monomer for forming polyanilines. In greater detail, the monomer for forming an electro-conductive polymer may be, for example, pyrrole, 3,4-ethylenedioxythiophene, styrene sulfonate, aniline, a derivative thereof, or a combination thereof.

The oxidizing agent is used to promote and/or enhance a mixing of a mixture of water and the polymer, and the monomer for forming an electro-conductive polymer. The mixture of water and the cross-linked polymer is usually immiscible or only partially miscible with the monomer for forming an electro-conductive polymer. On the contrary, the oxidizing agent is miscible with the mixture of water and the cross-linked polymer. Also, the oxidizing agent has an affinity to the monomer for forming an electro-conductive polymer. Accordingly, addition of the oxidizing agent facilitates and improves an uniform dispersion of the monomer for forming an electro-conductive polymer in a reaction mixture. As a result, even after cooling the reaction mixture and forming a reaction mixture gel, the monomer for forming an electro-conductive polymer may still be uniformly dispersed in the reaction mixture gel.

As the oxidizing agent, for example, $FeCl_3$, $CuCl_2$, $K_2S_2O_8$, or a combination thereof may be used.

An amount of the oxidizing agent in the reaction mixture may be, for example, about 40 parts by weight to about 300 parts by weight, based on 100 parts by weight of the cross-linked polymer cross-linked by hydrogen bonding. When the amount of the oxidizing agent is too small, the conductive polymer may not be sufficiently formed. When the amount of the oxidizing agent is too large, a residual oxidizing agent may be reduced at a high temperature to interfere with a reversible gelation of a hydrogel.

A heating temperature of the reaction mixture may be, for example, about 20° C. to about 40° C. When the heating temperature of the reaction mixture is too low, there is no particular problem, but a formation speed of the conductive polymer may be slow. When the heating temperature of the reaction mixture is too high, the reaction mixture (e.g. oxidizing agent) itself may be reduced, such that the oxidizing agent may not function as desired, i.e., resulting in a failure of a formation reaction of the conductive polymer.

A cooling temperature of the reaction mixture may be, for example, about 20° C. to about 25° C. When the cooling temperature of the reaction mixture is too low, gelation of the hydrogel may occur too fast, such that the conductive polymer may not be uniformly dispersed in the hydrogel. When the cooling temperature of the reaction mixture is too high, gelation of the hydrogel may not occur.

When the reaction mixture is cooled, the cross-linked polymer cross-linked by hydrogen bonding forms a cross-link network to form a reaction mixture gel. The monomer for forming an electro-conductive polymer dispersed in the reaction mixture gel gradually polymerizes to form an electro-conductive polymer. As a result, the electrical conductivity of the reaction mixture gel gradually increases as time progresses. After a certain period of time, the reaction mixture gel transforms into an electro-conductive hydrogel composite material having a desired level of electrical conductivity. A time taken to complete the polymerization of the monomer for forming an electro-conductive polymer dispersed in the reaction mixture gel may be, for example, about 30 minutes to about 2 weeks.

EXAMPLE

Example 1

0.45 M of Polypyrrole and Deionized Water 0.1 g of agarose and 1.52 g of $FeCl_3$ were dissolved in 5 g of deionized water at a temperature of 50° C. in a 20 ml beaker. Here, 0.3 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 30 minutes, such that the pyrrole monomers polymerize to form polypyrrole, thereby obtaining an electro-conductive hydrogel composite material of Example 1. Then, the beaker was held upside down, and it was confirmed that the prepared electro-conductive hydrogel composite material did not detach from the bottom of the beaker.

Example 2

0.15 M of Polypyrrole and Deionized Water 0.1 g of agarose and 0.51 g of $FeCl_3$ were dissolved in 5 g of deionized water at a temperature of 50° C. in a 20 ml beaker. Here, 0.1 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 120 minutes, such that the pyrrole monomers polymerize to form polypyrrole, to prepare an electro-conductive hydrogel composite material of Example 2. Then, the beaker was held upside down, to confirm that the prepared electro-conductive hydrogel composite material does not detach from the bottom of the beaker.

Example 3

0.074 M of Polypyrrole and Deionized Water 0.1 g of agarose and 0.25 g of $FeCl_3$ were dissolved in 5 g of deionized water at a temperature of 50° C. in a 20 ml beaker. Here, 0.05 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 300 minutes, such that the pyrrole monomers polymerize to form polypyrrole, to prepare an electro-conductive hydrogel composite material of Example 3. Then, the beaker was held upside down, to confirm that the prepared electro-conductive hydrogel composite material does not detach from the bottom of the beaker.

Example 4

0.01 M of Polypyrrole and Deionized Water 0.1 g of agarose and 0.10 g of $FeCl_3$ were dissolved in 5 g of deionized water at a temperature of 50° C. in a 20 ml beaker. Here, 0.02 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 140 minutes, such that the pyrrole monomers polymerize to form polypyrrole, to prepare an electro-conductive hydrogel composite material of Example 4. Then, the beaker was held upside down, to confirm that the prepared electro-conductive hydrogel composite material does not detach from the bottom of the beaker.

Comparative Example 1

0.00 M of Polypyrrole and Deionized Water 0.1 g of agarose was dissolved in 5 g of deionized water at a temperature of 50° C. in a 20 ml beaker to obtain an agarose aqueous solution. Thereafter, the agarose aqueous solution at a temperature of 50° C. in the beaker was cooled to a temperature of 25° C. to form a non-electro-conductive agarose hydrogel of Comparative Example 1. Then, the beaker was held upside down, and it was confirmed that the prepared non-electro-conductive agarose hydrogel did not detach from the bottom of the beaker.

Example 5

0.45 M of polypyrrole and 10×PBS

First, 10×PBS was prepared. A composition of 1 L of the 10×PBS 1 included 80 g of NaCl, 2 g of KCl, 14.4 g of $Na_2HPO_4$, 2.4 g of $KH_2PO_4$, and a residual amount of deionized water. A pH of the 10×PBS was 7.4. 0.1 g of agarose and 1.52 g of $FeCl_3$ were dissolved in 5 g of 10×PBS at a temperature of 50° C. in a 20 ml beaker. Here, 0.3 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 30 minutes, such that the pyrrole monomers polymerize to form polypyrrole, to prepare an electro-conductive hydrogel composite material of Example 5. Then, the beaker was held upside down, to confirm that the prepared electro-conductive hydrogel composite material does not detach from the bottom of the beaker.

Example 6

0.15 M of Polypyrrole and 10×PBS 0.1 g of agarose and 0.51 g of $FeCl_3$ were dissolved in 5 g of 10×PBS at a temperature of 50° C. in a 20 ml beaker. Here, 0.1 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 120 minutes, such that the pyrrole monomers polymerize to form polypyrrole, to prepare an electro-conductive hydrogel composite material of Example 6. Then, the beaker was held upside down, to confirm that the prepared electro-conductive hydrogel composite material does not detach from the bottom of the beaker.

Example 7

0.074 M of Polypyrrole and 10×PBS 0.1 g of agarose and 0.25 g of $FeCl_3$ were dissolved in 5 g of 10×PBS at a temperature of 50° C. in a 20 ml beaker. Here, 0.05 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 300 minutes, such that the pyrrole monomers polymerize to form polypyrrole, to prepare an electro-conductive hydrogel composite material of Example 7. Then, the beaker was held upside down, to confirm that the prepared electro-conductive hydrogel composite material does not detach from the bottom of the beaker.

Example 8

0.03 M of Polypyrrole and 10×PBS 0.1 g of agarose and 0.10 g of $FeCl_3$ were dissolved in 5 g of 10×PBS at a temperature of 50° C. in a 20 ml beaker. Here, 0.02 g of pyrrole monomers was added and then stirred to obtain a reaction mixture. Thereafter, the reaction mixture at a temperature of 50° C. in the beaker was cooled to a temperature of 25° C. to form a reaction mixture gel. Then, the reaction mixture gel was allowed to sit at a temperature of 25° C. for 140 minutes, such that the pyrrole monomers polymerize to form polypyrrole, to prepare an electro-conductive hydrogel composite material of Example 8. Then, the beaker was held upside down, to confirm that the prepared electro-conductive hydrogel composite material does not detach from the bottom of the beaker.

Comparative Example 2

0.00 M of Polypyrrole and 10×PBS 0.1 g of agarose was dissolved in 5 g of 10×PBS at a temperature of 50° C. in a 20 ml beaker to obtain an agarose aqueous solution. Thereafter, the agarose aqueous solution at a temperature of 50° C. in the beaker was cooled to a temperature of 25° C. to form a non-electro-conductive agarose hydrogel of Comparative Example 2. Then, the beaker was held upside down, to confirm that the prepared non-electro-conductive agarose hydrogel does not detach from the bottom of the beaker.

<Evaluation Results>
Morphology

The agarose hydrogel (amount of polypyrrole: zero) of Comparative Example 1, the electro-conductive hydrogel composite material (amount of polypyrrole: 0.15 M) of Example 2, and the electro-conductive hydrogel composite material (amount of polypyrrole: 0.45 M) of Example 1 were freeze-dried under vacuum conditions. Freeze-dried samples were analyzed under a scanning electron microscope (SEM).

Figure 2:
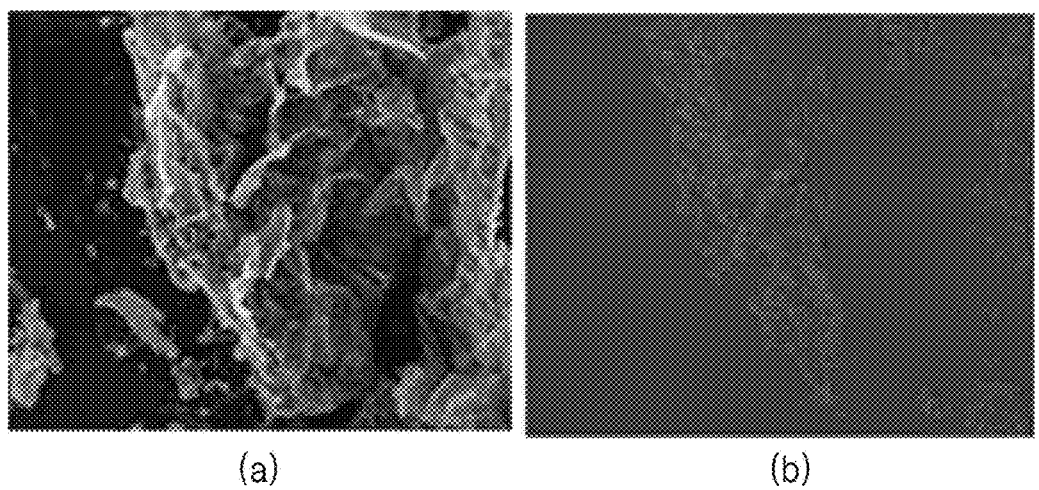
FIG. 2(a) is a SEM image and 2(b) is a nitrogen mapping image from an energy dispersive X-ray analysis (EDX) of the electro-conductive hydrogel composite material of Example 2.
Figure 3:
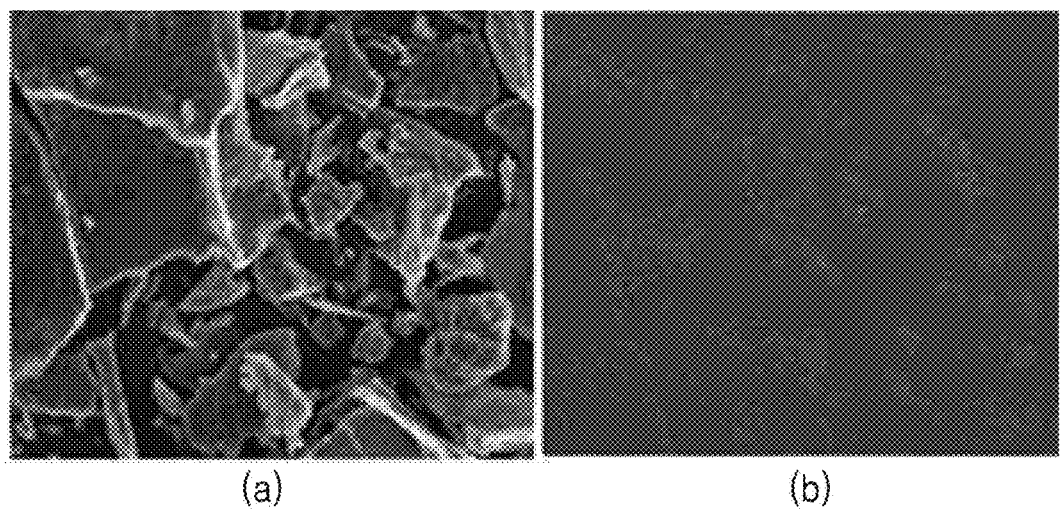
FIG. 3(a) is a SEM image and 3(b) is a nitrogen mapping image from an EDX of the electro-conductive hydrogel composite material of Example 1.

FIG. 1 are SEM images of freeze-dried (a) agarose hydrogel of Comparative Example 1, (b) electro-conductive hydrogel composite material of Example 2, and (c) electro-conductive hydrogel composite material of Example 1. FIG. 1(a) only shows an agarose polymer structure. FIGS. 1(b) and (c) show an agarose polymer structure together with a polypyrrole particle. FIG. 2 is (a) a SEM image and (b) a nitrogen mapping image from an energy dispersive X-ray analysis (EDX) of the electro-conductive hydrogel composite material of Example 2. White spots in FIG. 2(b) indicate locations of nitrogen atoms of the polypyrrole. It may be concluded from FIG. 2(b) that the polypyrroles are thoroughly dispersed. FIG. 3 is (a) a SEM image and (b) a nitrogen mapping image from an EDX of the electro-conductive hydrogel composite material of Example 1. White spots in FIG. 3(b) indicate locations of nitrogen atoms of the polypyrrole. It may be concluded from FIG. 3(b) that the polypyrroles are thoroughly dispersed.

As shown in FIGS. 1 to 3, as an amount of the polypyrrole increased, a shape of an agarose polymer nanostructure transformed from a leaf shape to a hard cone shape. Also, as the amount of the polypyrrole increased, a distribution of the polypyrrole was broader in the electro-conductive hydrogel composite material.

Electrical Conductivity

Figure 4:
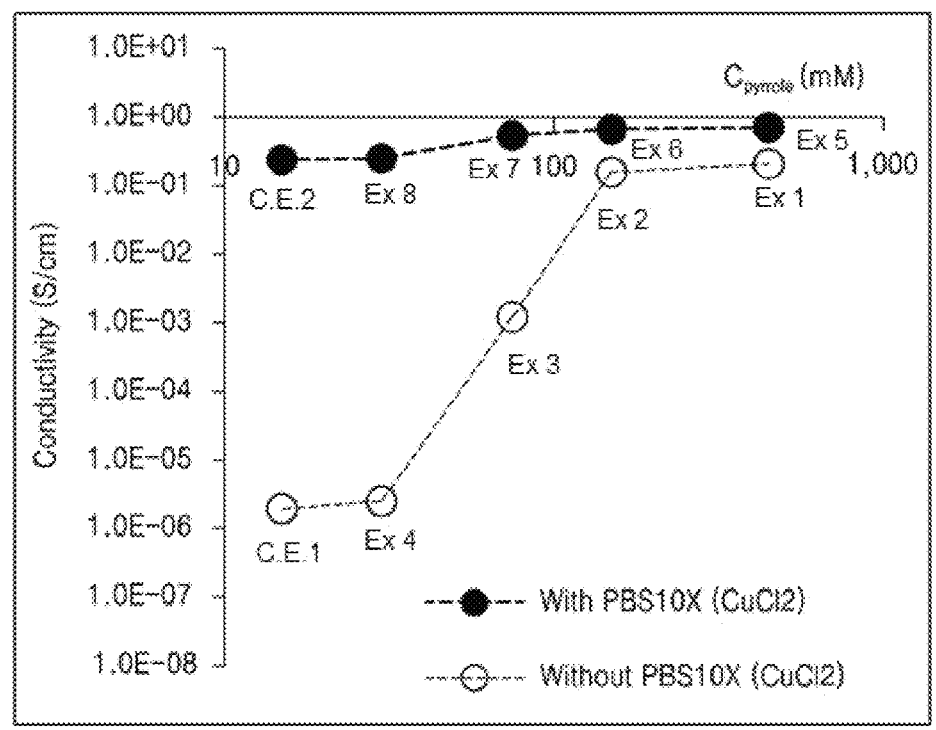
FIG. 4 is a graph showing electrical conductivity of the electro-conductive hydrogel composite materials of Examples 1-8, and the agarose hydrogels of Comparative Examples 1 and 2.

Electrical conductivities of the electro-conductive hydrogel composite materials of Examples 1 to 8, and the agarose hydrogels of Comparative Examples 1 and 2 were measured by using a 4-probe method and under standard conditions (temperature of 25° C. and pressure of 1 atm-absolute). FIG. 4 is a graph showing electrical conductivity of the electro-conductive hydrogel composite materials of Examples 1-8, and the agarose hydrogels of Comparative Examples 1 and 2. As shown in FIG. 4, as the amount of polypyrrole in the hydrogel increased, numerous pathways for electrical conductivity were formed in the hydrogel, such that the electrical conductivity of the hydrogel increased up to 0.2 S/cm at maximum. When an electrolyte was added to water in the hydrogel, ion conductivity was generated due to the electrolyte, in addition to electronic conductivity generated by the polypyrrole, thereby further improving the electrical conductivity of the hydrogel. As shown in FIG. 4, the electrical conductivity of the hydrogel that included 10×PBS and the electrolyte was about 0.2 S/cm to about 0.7 S/cm greater than the electrical conductivity of the hydrogel that included deionized water.

Healing Property

Figure 5:
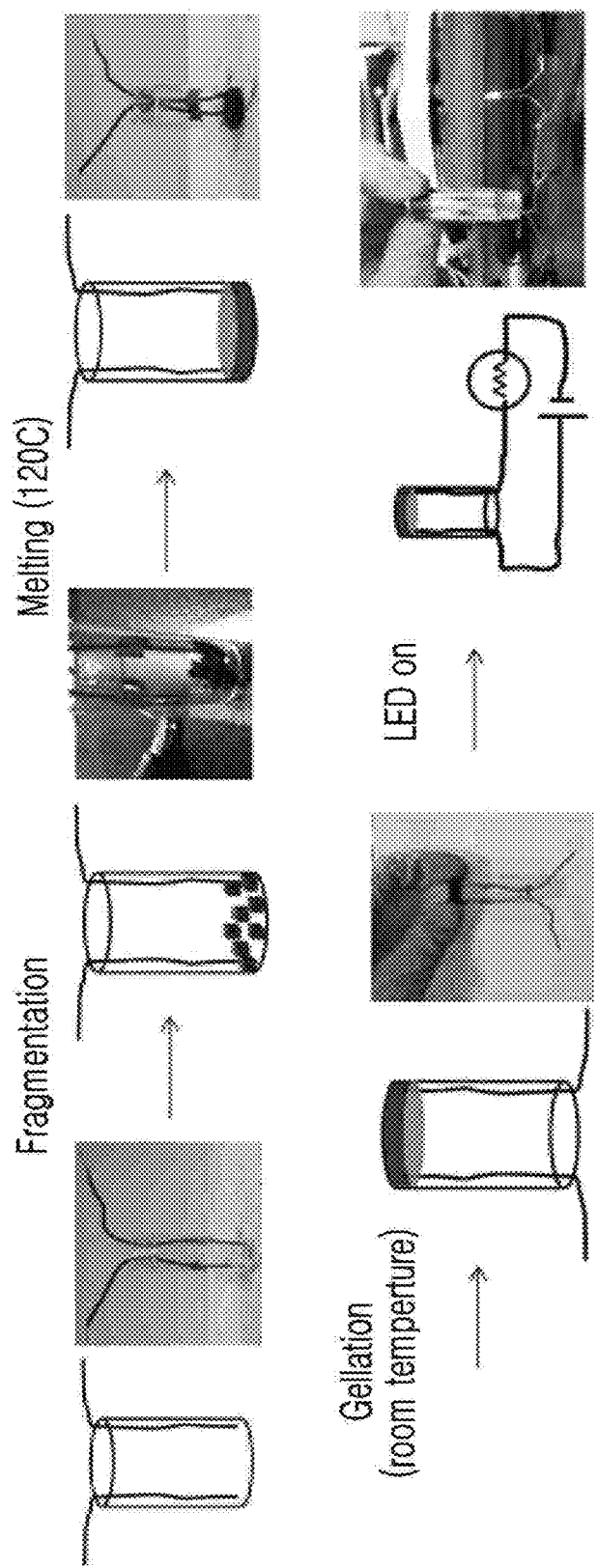
FIG. 5 shows experimental steps performed to identify thermal healing properties of the electro-conductive hydrogel composite material.

FIG. 5 shows experimental steps performed to confirm thermal healing properties of the electro-conductive hydrogel composite material. An electro-conductive hydrogel composite material obtained in Example 5 was split into pieces, and the electro-conductive hydrogel composite material pieces were heated to a temperature of 120° C. to transform the hydrogel composite material pieces into a sol state. The electro-conductive hydrogel composite material pieces that were transformed into the sol state stick to each other as they flowed. Then, the electro-conductive hydrogel composite material pieces that were transformed into the sol state were cooled to a temperature of 25° C. and then re-gelled. As confirmed by lights on a LED, the re-gelled electro-conductive hydrogel composite material still maintained electrical conductivity. That is, when the electro-conductive hydrogel composite material is damaged, the electro-conductive hydrogel composite material may be thermally healed.

Changes in the Limit of Healing Cycles According to an Amount of Polypyrrole

The electro-conductive hydrogel composite materials prepared in Examples 9 to 11, which were prepared in the same manner as in Example 1 except for varying the amount of the polypyrrole, were subjected to 10 cycles of heating at a temperature of 120° C. and cooling at a temperature of 25° C. Results are summarized in Table 1 below.

TABLE 1

| Number of cycles | Example 11 Amount of polypyrrole: 0.015 M | Example 10 Amount of polypyrrole: 0.045 M | Example 9 Amount of polypyrrole: 0.075 M |
|---|---|---|---|
| 1 | Re-gelled | Re-gelled | Re-gelled |
| 2 | Re-gelled | Re-gelled | Re-gelled |
| 3 | Re-gelled | Re-gelled | Re-gelled |
| 4 | Re-gelled | Re-gelled | Not re-gelled |
| 5 | Re-gelled | Not re-gelled | Not re-gelled |
| 6 | Re-gelled | Not re-gelled | Not re-gelled |
| 7 | Re-gelled | Not re-gelled | Not re-gelled |
| 8 | Re-gelled | Not re-gelled | Not re-gelled |
| 9 | Re-gelled | Not re-gelled | Not re-gelled |
| 10 | Re-gelled | Not re-gelled | Not re-gelled |

As shown in Table 1 above, when the amount of the polypyrrole increases beyond a certain point, the number of thermal healing cycles of the electro-conductive hydrogel composite material may be suddenly reduced. For example, when the amount of the polypyrrole was 15 mM, the electro-conductive hydrogel composite material successfully re-gelled (healed) after 10 cycles of heating at a temperature of 120° C. and cooling at a temperature of 25° C. However, when the amount of the polypyrrole was 45 mM, the electro-conductive hydrogel composite material became unable to re-gel only after repeating 4 cycles of heating at 120° C. and cooling at 25° C.

Flexibility

Figure 6:
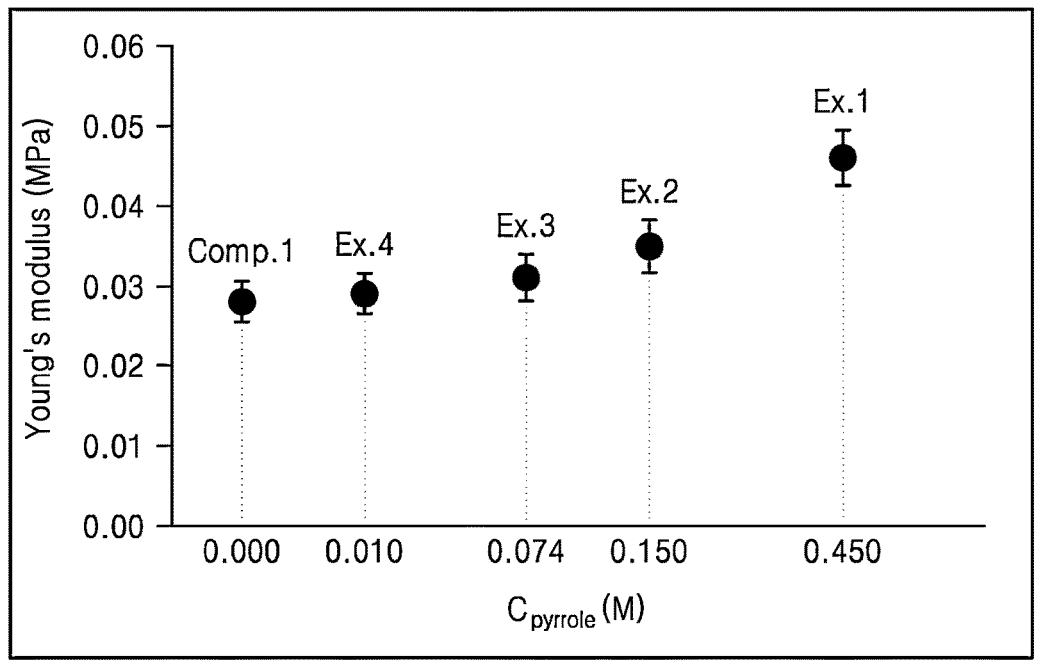
FIG. 6 is a graph showing the Young's modulus of the electro-conductive hydrogel composite materials of Examples 1 to 4 and the agarose hydrogel of Comparative Example 1.

A uniaxial tensile test was performed for the electro-conductive hydrogel composite materials of Examples 1 to 4 and the agarose hydrogel of Comparative Example 1 to measure the Young's modulus. Results are shown in FIG. 6. FIG. 6 is a graph showing the Young's modulus of the electro-conductive hydrogel composite materials of Examples 1 to 4 and the agarose hydrogel of Comparative Example 1. When the amount of the polypyrrole increased, the Young's modulus increased from 27 kPa to 46 kPa. Human skin has a Young's modulus of about 400 kPa to about 800 kPa. As a result, it may be concluded that the electro-conductive hydrogel composite materials of Examples 1 to 4 have similar flexibility to human skin.

Breakage Strain

Figure 7:
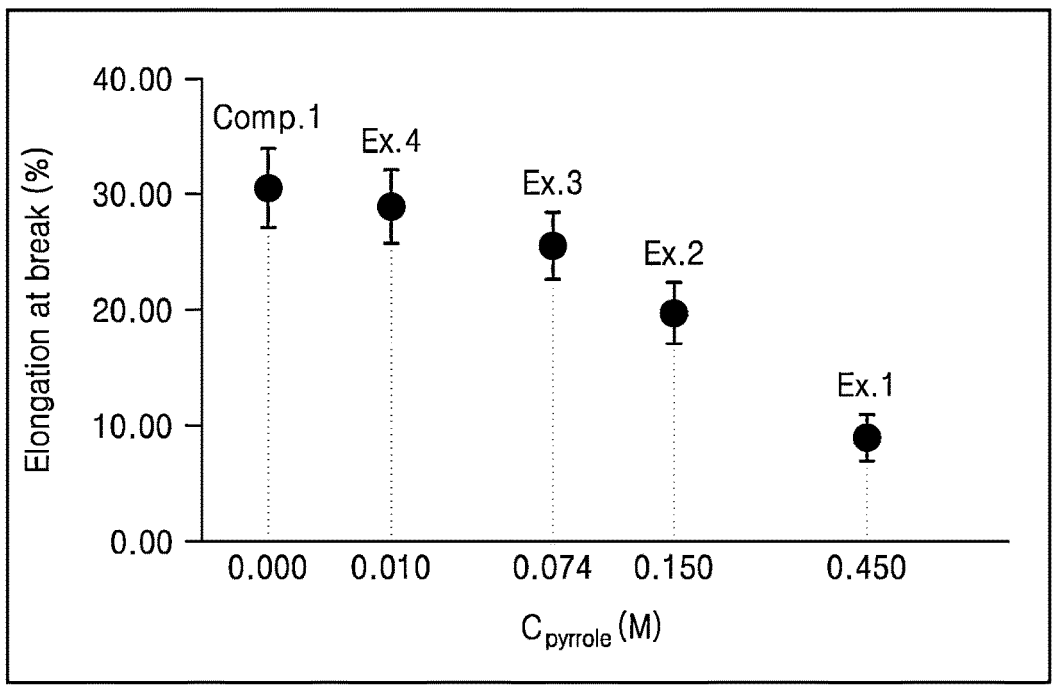
FIG. 7 is a graph showing breakage strain measured through an uniaxial tensile test of the electro-conductive hydrogel composite materials of Examples 1 to 4, and the agarose hydrogel of Comparative Example 1.

A uniaxial tensile test was performed for the electro-conductive hydrogel composite materials of Examples 1 to 4 and the agarose hydrogel of Comparative Example 1 to measure breakage strain. Results are shown in FIG. 7. As shown in FIG. 7, the electro-conductive hydrogel composite material may break even under very low elongation when too much polypyrrole is included therein.

Electrical Conductivity after Elongation

Figure 8:
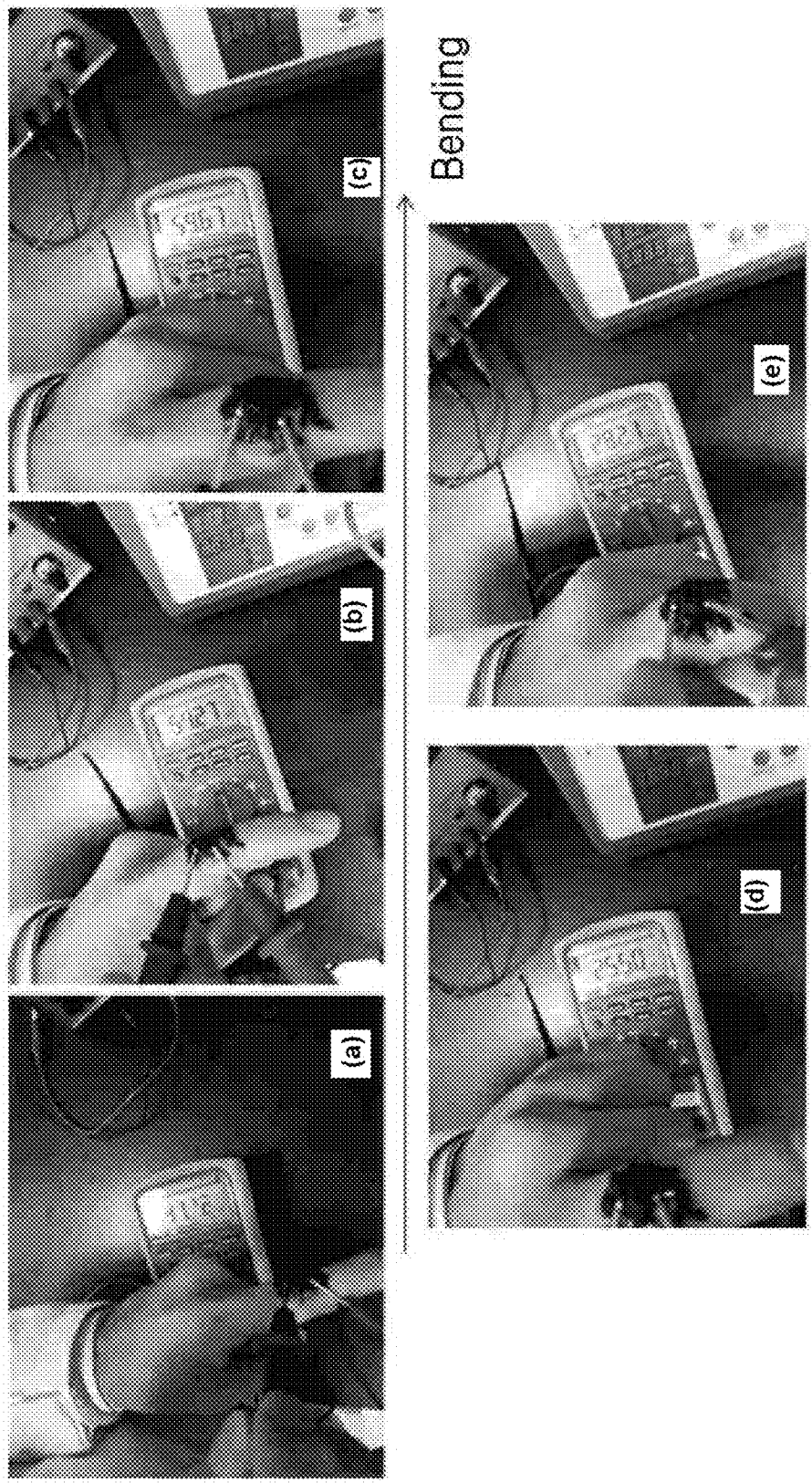
FIG. 8(*a*)-(*e*) show experimental steps for measuring electrical conductivity after elongation of the electro-conductive hydrogel composite material of Example 1.
Figure 9:
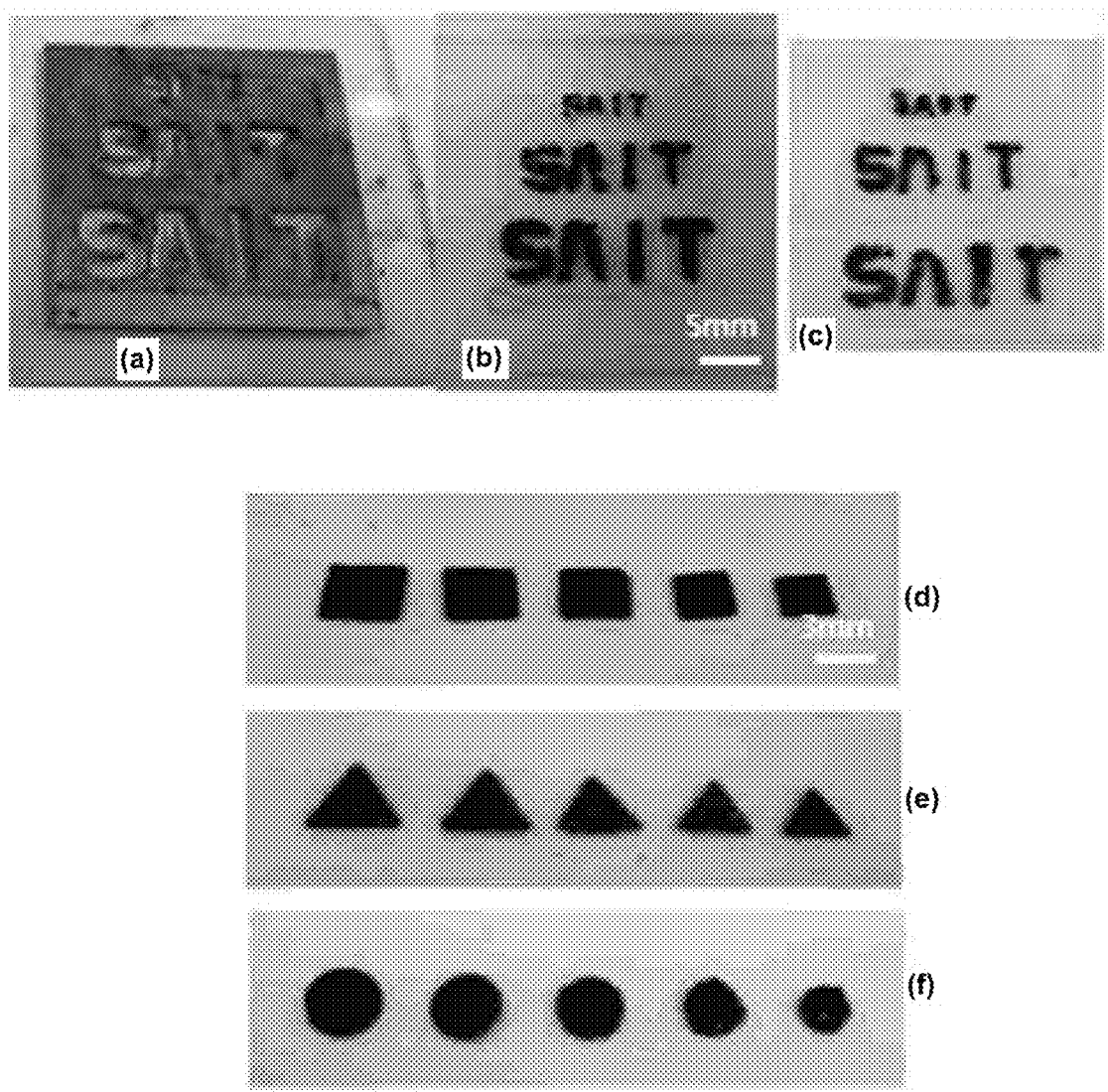
FIG. 9(*a*)-(*f*) show results of patterning the electro-conductive hydrogel composite material of Example 1 through a screen printing method.

FIG. 8 shows experimental processes for measuring electrical conductivity after elongation of the electro-conductive hydrogel composite material of Example 1. That is, the electro-conductive hydrogel composite material was applied to a finger joint, and the finger joint was bent to measure the electrical resistance of an elongated electro-conductive hydrogel composite material. Agarose is a biocompatible material and thus, the electro-conductive hydrogel composite material of Example 1 is non-toxic to skin and may be applied to skin. As shown in FIG. 8(a)-(e), the electro-conductive hydrogel composite material was electrically conductive even when the finger joint was bent. The electrical resistance of the elongated electro-conductive hydrogel composite material when the finger joint was bent (282 kohm) was about 6.5 times as great as the electrical resistance of the unelongated electro-conductive hydrogel composite material when the finger joint was straight (41 kohm). However, even after elongated, the electro-conductive hydrogel composite material of Example 1 still showed electrical conductivity.

Formability

Figure 10:
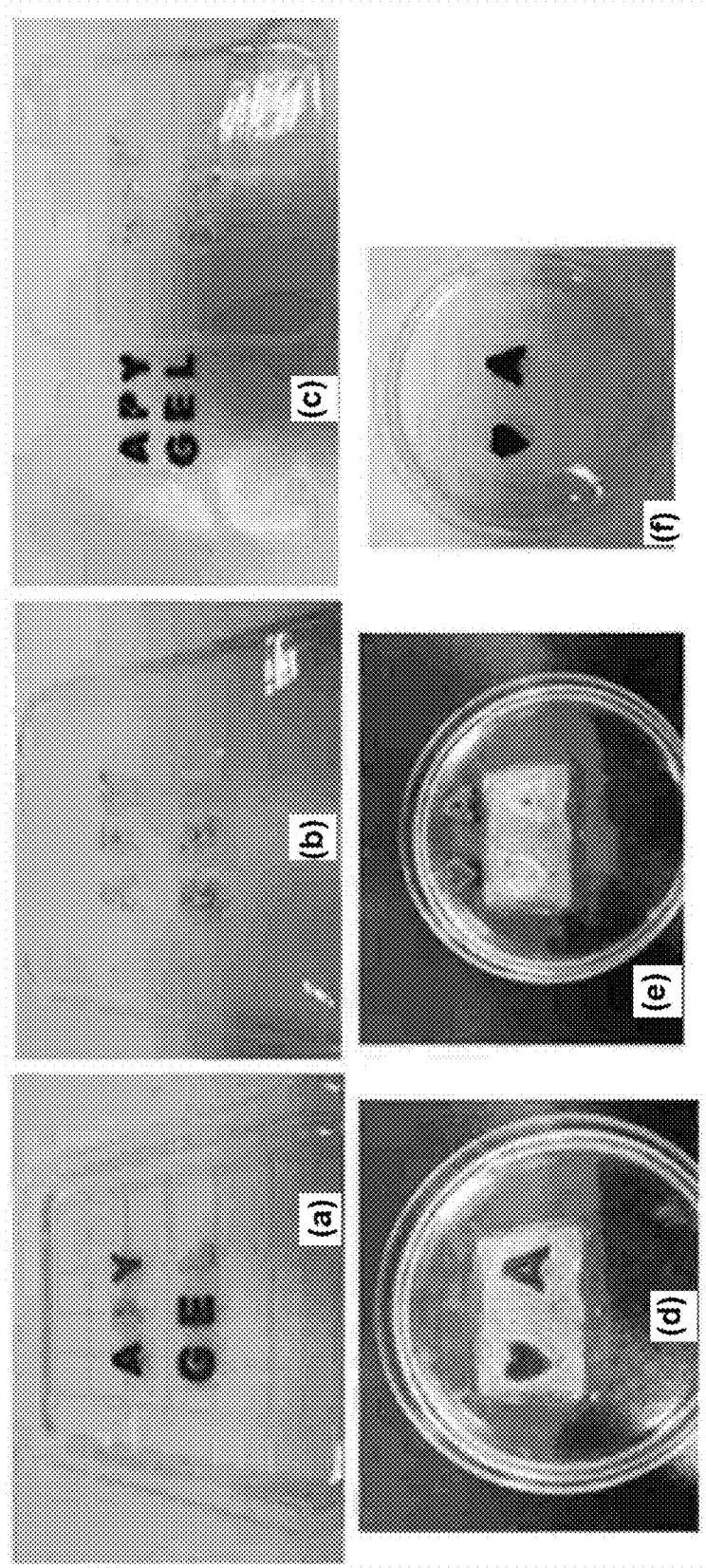
FIG. 10(*a*)-(*f*) show results of manufacturing the electro-conductive hydrogel composite material of Example 1 into a free-standing figure by a molding method.
Figure 11:
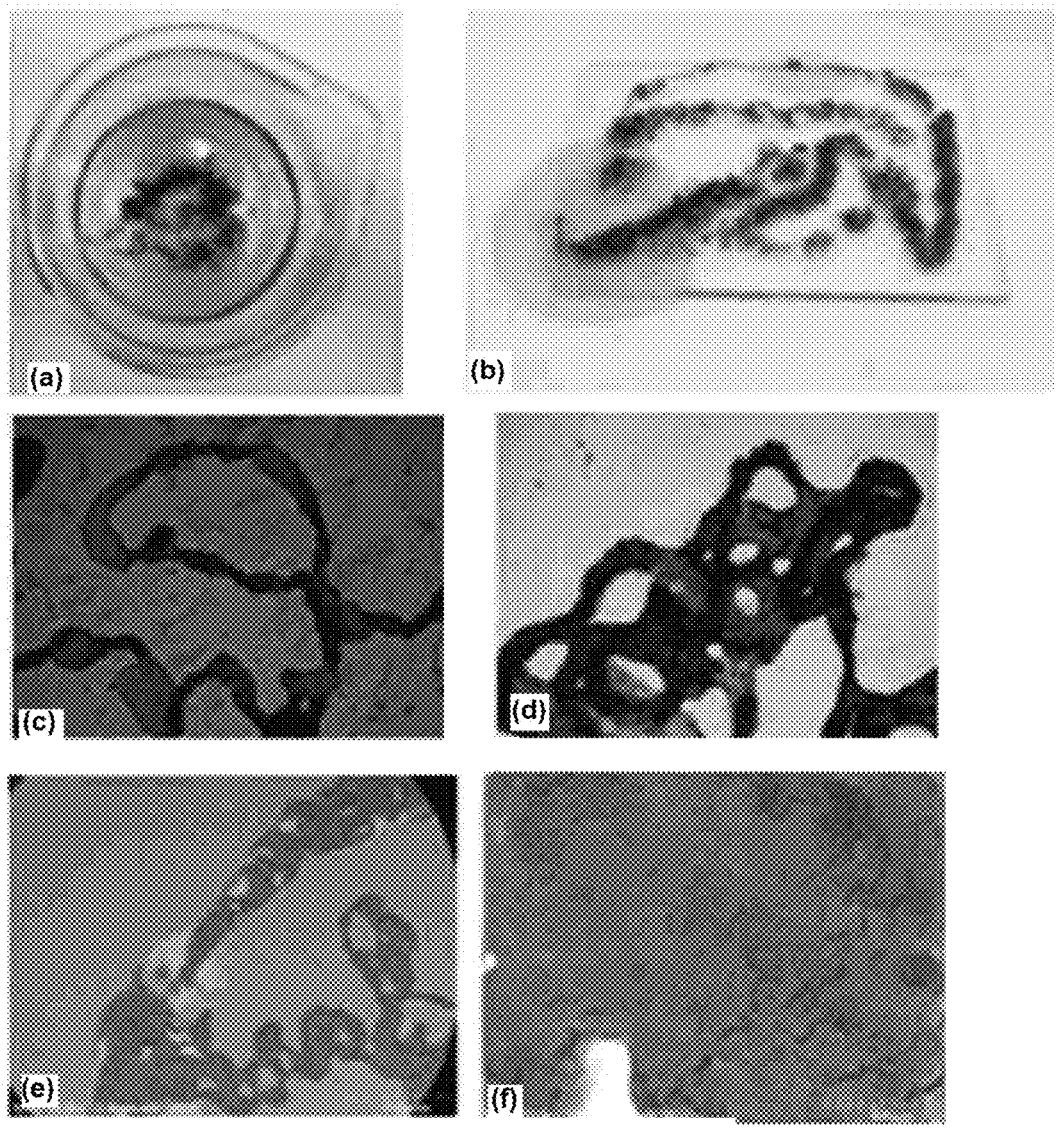
FIG. 11(*a*)-(*f*) show results of manufacturing fibers through a wet spinning method by using the electro-conductive hydrogel composite material of Example 1.

When the electro-conductive hydrogel composite material of the present disclosure is heated, the electro-conductive hydrogel composite material transforms into a sol state to have fluidity, and when cooled, the electro-conductive hydrogel composite material is re-gelled and loses fluidity. Accordingly, the electro-conductive hydrogel composite material of the present disclosure may be formed by using various methods. FIG. 9(a)-(f) show results of patterning the electro-conductive hydrogel composite material of Example 1 through a screen printing method. FIG. 10 shows results of manufacturing the electro-conductive hydrogel composite material of Example 1 into a free-standing figure by a molding method. FIG. 11 shows results of manufacturing fibers through a wet spinning method by using the electro-conductive hydrogel composite material of Example 1.

As described above, according to the one or more of the above embodiments of the present invention, the electro-conductive hydrogel composite material may satisfy all of four requirements of artificial skin, namely, "flexibility," "electrical conductivity," "healing property," and "biocompatibility."

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An electro-conductive hydrogel composite material comprising:
   a hydrogel composition comprising (a) water and (b) a cross-linkable polymer, said polymer reversibly forming a cross-linkage by hydrogen bonding; and
   an electro-conductive material dispersed in the hydrogel composition,
   wherein the electro-conductive hydrogel composite material is a thermally healable skin.

2. The electro-conductive hydrogel composite material of claim 1, wherein the cross-linkable polymer is agarose.

3. The electro-conductive hydrogel composite material of claim 1, wherein an amount of the water in the hydrogel composition is about 0.5 parts by weight to about 5.0 parts by weight based on 100 parts by weight of the cross-linkable polymer.

4. The electro-conductive hydrogel composite material of claim 1, wherein the electro-conductive material is a metal particle, a conductive carbon material, a conductive polymer, or a combination thereof.

5. The electro-conductive hydrogel composite material of claim 4, wherein the metal is a metal element or a metal compound wherein the metal is selected from the group consisting of gold, silver, platinum, titanium, iron, and a combination thereof.

6. The electro-conductive hydrogel composite material of claim 4, wherein the conductive carbon material is carbon black, carbon nanotubes, graphene, or a combination thereof.

7. The electro-conductive hydrogel composite material of claim 4, wherein the conductive polymer is polypyrroles, poly(3,4-ethylenedioxythiophenes), poly(styrenesulfonates), poly(3,4-ethylenedioxythiophenes):poly(styrenesulfonates), polyanilines, or a combination thereof.

8. The electro-conductive hydrogel composite material of claim 1, wherein the electro-conductive material has an average particle size of about 100 nm to about 1 μm.

9. The electro-conductive hydrogel composite material of claim 1, wherein an amount of the electro-conductive material in the hydrogel composition is about 10 parts by weight to about 300 parts by weight based on 100 parts by weight of the cross-linkable polymer.

10. The electro-conductive hydrogel composite material of claim 1, wherein the water further comprises an electrolyte.

11. The electro-conductive hydrogel composite material of claim 10, wherein the electrolyte is NaCl, KCl, $Na_2HPO_4$, $KH_2PO_4$, $Na_2SO_4$, $Li_2SO_4$, $MgSO_4$, phosphate-buffered saline buffer, Tris-HCl buffer, or a combination thereof.

12. The electro-conductive hydrogel composite material of claim 10, wherein an amount of the electrolyte is about 0.1 parts by weight to about 5.0 parts by weight based on 100 parts by weight of the water in the hydrogel composition.

13. The electro-conductive hydrogel composite material of claim 10, wherein the water which comprises an electrolyte is phosphate-buffered saline.

14. The electro-conductive hydrogel composite material of claim 1, wherein the electro-conductive material is polypyrrole, and an amount of the polypyrrole is greater than 0 parts by weight and equal to or less than about 300 parts by weight based on 100 parts by weight of the cross-linkable polymer.

15. A method of preparing an electro-conductive hydrogel composite material, comprising
providing a heated dispersion comprising a cross-linkable polymer which reversibly forms cross linkages by hydrogen bonding, water, and an electro-conductive material; and
cooling the dispersion to a temperature such that the dispersion forms a hydrogel in which the conductive material is dispersed,
wherein the electro-conductive hydrogel composite material is a thermally healable skin.

16. A method of preparing an electro-conductive hydrogel composite material comprising (i) a hydrogel comprising water and a cross-linkable polymer which reversibly forms cross linkages by hydrogen bonding; and (ii) an electro-conductive polymer dispersed in the hydrogel, the method comprising:
providing a heated mixture comprising the cross-linkable polymer; water; a monomer for forming an electro-conductive polymer; and an oxidizing agent; and
cooling the mixture to a temperature such that the dispersion forms a hydrogel,
wherein the electro-conductive hydrogel composite material is a thermally healable skin.

17. The method of claim 16, wherein the oxidizing agent is $FeCl_3$, $CuCl_2$, $K_2S_2O_8$, or a combination thereof.

18. The method of claim 16, wherein an amount of the oxidizing agent in the reaction mixture is about 50 parts by weight to about 1500 parts by weight based on 100 parts by weight of the cross-linkable polymer capable of being cross-linked by hydrogen bonding.

19. An electro-conductive hydrogel composite material comprising:
a hydrogel composition comprising (a) an aqueous base and (b) agarose; and
a polypyrrole dispersed in the hydrogel composition,
wherein the electro-conductive hydrogel composite material is a thermally healable skin.

20. The electro-conductive hydrogel composite material of claim 19, wherein the aqueous base is water or a phosphate-buffered saline.

* * * * *